(12) United States Patent
Kim et al.

(10) Patent No.: US 8,518,853 B2
(45) Date of Patent: Aug. 27, 2013

(54) NANOMETER-SIZED COPPER-BASED CATALYST, PRODUCTION METHOD THEREOF, AND ALCOHOL PRODUCTION METHOD USING THE SAME THROUGH DIRECT HYDROGENATION OF CARBOXYLIC ACID

(75) Inventors: Hee Soo Kim, Daejeon (KR); Seong Ho Lee, Seoul (KR); Young Seek Yoon, Gwangju (KR); Seung Hoon Oh, Seoul (KR); Young Min Chung, Daejeon (KR); Ok Youn Kim, Daejeon (KR); Hee Jung Jeon, Daejeon (KR)

(73) Assignee: SK Innovation Co., Ltd., Seoul (KR)

( * ) Notice: Subject to any disclaimer, the term of this patent is extended or adjusted under 35 U.S.C. 154(b) by 0 days.

(21) Appl. No.: 13/641,813

(22) PCT Filed: Apr. 21, 2011

(86) PCT No.: PCT/KR2011/002874
§ 371 (c)(1),
(2), (4) Date: Oct. 17, 2012

(87) PCT Pub. No.: WO2011/132957
PCT Pub. Date: Oct. 27, 2011

(65) Prior Publication Data
US 2013/0030224 A1 Jan. 31, 2013

(30) Foreign Application Priority Data

Apr. 21, 2010 (KR) .................. 10-2010-0036679
Jul. 27, 2010 (KR) .................. 10-2010-0072312

(51) Int. Cl.
*B01J 23/60* (2006.01)
*B01J 23/70* (2006.01)

(52) U.S. Cl.
USPC ............ 502/342; 502/318; 502/329; 502/331

(58) Field of Classification Search
USPC ................. 502/342, 318, 329, 331
See application file for complete search history.

(56) References Cited

U.S. PATENT DOCUMENTS

| | | | |
|---|---|---|---|
| 4,990,655 | A | 2/1991 | Kitson et al. |
| 7,084,312 | B1 | 8/2006 | Huber et al. |
| 7,119,237 | B2 | 10/2006 | Prinz et al. |
| 8,088,708 | B2 | 1/2012 | Takatsu et al. |
| 2008/0248540 | A1 | 10/2008 | Yang |
| 2010/0121114 | A1 | 5/2010 | Weiner et al. |
| 2011/0294176 | A1 | 12/2011 | Kang et al. |

FOREIGN PATENT DOCUMENTS

| | | |
|---|---|---|
| JP | 2007-083197 A | 4/2007 |
| JP | 2009-215322 A | 9/2009 |
| KR | 10-2002-0025257 A | 4/2002 |
| KR | 10-2007-0028102 A | 3/2007 |
| KR | 10-2009-0049656 A | 5/2009 |
| KR | 10-2009-0103720 A | 10/2009 |
| KR | 10-2009-0128460 A | 12/2009 |
| KR | 10-2010-0006249 A | 1/2010 |
| WO | 2008/070561 A1 | 6/2008 |

OTHER PUBLICATIONS

PCT International Search Report, PCT/KR2011/002874, Jan. 12, 2012, pp. 1-4.

*Primary Examiner* — Elvis O Price
(74) *Attorney, Agent, or Firm* — Abelman, Frayne & Schwab (57) ABSTRACT

Disclosed is a nano-sized Cu based catalyst and a method of preparing the same including dissolving, in an aqueous solution, a first component comprising a Cu precursor, a second component precursor comprising one or more selected from the group consisting of a transition metal, an alkaline earth metal and a Group IIIb metal, and a third component precursor comprising one or more selected from the group consisting of alumina, silica, silica-alumina, magnesia, titania, zirconia and carbon and then performing stirring; precipitating the stirred mixture solution using $Na_2CO_3$ and NaOH to form a catalyst precursor precipitate; and washing and filtering the formed catalyst precursor precipitate. Also a method of preparing alcohol is provided, including reacting hydrogen with carboxylic acid including a single acid or an acid mixture of two or more acids derived from a microorganism fermented solution, using the nano-sized Cu based catalyst.

14 Claims, 9 Drawing Sheets

NANOMETER-SIZED COPPER-BASED CATALYST, PRODUCTION METHOD THEREOF, AND ALCOHOL PRODUCTION METHOD USING THE SAME THROUGH DIRECT HYDROGENATION OF CARBOXYLIC ACID

RELATED APPLICATIONS

This application is a United States national phase application under 35 USC §371 of PCT/KR2011/002874 filed on Apr. 21, 2011, and claims the benefit under 35 USC §119 of Korean patent application numbers KR 10-2010-0036679 filed Apr. 21, 2010 and KR 10-2010-0072312 filed Jul. 27, 2010, the disclosures of which are all incorporated herein by reference in their entireties.

TECHNICAL FIELD

The present invention relates to a nano-sized Cu based catalyst and a method of preparing the same, and more particularly to a method of preparing Cu particles the size of which is controlled to the level of tens of nm or smaller using a specific precipitant and to a method of preparing a single alcohol or an alcohol mixture by reacting carboxylic acid comprising a single acid or an acid mixture of two or more acids derived from a microorganism fermented solution, with hydrogen, using the Cu based catalyst.

BACKGROUND ART

When Cu is used as a catalyst, it is typically active in hydrogenation-dehydrogenation reactions. Cu metal which is activated in an atomic state by dissociative adsorption of hydrogen molecule thereon may be used as an active material for hydrogenation along with a noble metal such as Pt, Pd, Re or the like. If the hydrogen adsorption strength of the active material for hydrogenation is too large, it may be hydrocracked, and is undesirably hydrogenated while breaking the C—C bond of the hydrocarbon. Hence, it is necessary that hydrogen be appropriately adsorbed.

The Cu based catalyst is applied to hydrogenation or dehydrogenation in the relatively low temperature range (200-400° C.). In particular, the Cu based catalyst is known to have superior capability in terms of hydrogenation for synthesizing alcohol from carboxylic acid, water-gas shift reaction for making synthesis gas of carbon monoxide and hydrogen from hydrocarbon and water or carbon and water, methanol reforming for producing hydrogen from methanol and $CO_2$ hydrogenation for synthesizing methanol from hydrogen and $CO_2$ as opposed thereto, hydrodechlorination for removing Cl from Cl-containing hydrocarbon, and production of γ-butyrolactone from 1,4-butanediol (1,4-BDO).

Also a variety of methods of preparing a Cu based catalyst are known. Korean Laid-open Patent Publication No. 2010-0006249 discloses a heterogeneous Cu nanocatalyst, a method of preparing the same, and the use thereof in which the heterogeneous nanocatalyst includes Cu nanoparticles immobilized to a boehmite support.

Korean Laid-open Patent Publication No. 2007-0028102 discloses a method of preparing a nano-sized Cu—Mn oxide catalyst, comprising dissolving a manganese nitrate hydrate and a copper nitrate hydrate in distilled water, adding urea to the resulting solution so that urea is dissolved therein, adding a support to the solution with stirring in a neutral atmosphere, and drying, grinding and burning the stirred solution.

However, methods of efficiently preparing the nano-sized Cu based catalyst are still insufficient.

On the other hand, carboxylic acid obtained from fermenting biomass is used as a starting material for the preparation of alcohol, ketone, ester, and aldehyde, and is regarded as important in the chemical and energy industries. In particular, alcohol which is being increasingly used as a fuel as well as a chemical material is produced in a larger amount by a biological process including fermenting biomass which is environmentally friendly, in the production of petrochemicals.

The process of preparing alcohol comprising pretreating biomass and fermenting it requires a relatively long period of time because the biomass is converted into alcohol via a carboxylate using a pure biological process.

US Patent Application No. 2008/0248540 discloses the use of biological fermentation and chemical conversion via catalysis thus increasing the production yield of butanol and shortening the preparation time. In particular, butyric acid resulting from fermentation is esterified and then reacted with alcohol in the presence of an acid catalyst, thus preparing alkylbutyrate ester, which is then hydrogenated in a high-pressure hydrogen atmosphere using hydrocracking, thereby preparing the corresponding alcohol.

When butanol is prepared from butyric acid, butyric acid is reacted with butanol to form butyric acid butyl ester (or butylbutyrate), followed by performing hydrocracking thereby preparing butanol, which is represented below.

1 Step: butyric acid+butanol→butyric acid butyl ester+water (esterification)
2 Step: butyric acid butyl ester+hydrogen→butanol (hydrocracking)

The above esterification is carried out under low temperature (100-200° C.) and low pressure (5 bar) conditions using a batch reactor or a continuous flow reactor in the presence of an acid catalyst such as an ion exchange resin catalyst, a zeolite catalyst or the like, and the hydrocracking is carried out in a high-pressure hydrogen atmosphere. Thus, the preparation of butanol from butyric acid is conducted through two-step catalytic reactions and the catalysts used in the respective reactions should have different functions.

Because alcohol used for the esterification is excessively supplied from the outside (the molar ratio of alcohol/butyric acid=5 or more), the volume of the reactor should be increased and an additional process for separating, purifying and re-circulating the unreacted alcohol is required. In particular, the equilibrium conversion of the esterification depends on the reaction conditions and thus in order to increase the yield of butanol it is important that the reaction conditions be set so that a high equilibrium conversion is ensured. Also in the hydrocracking, the reaction becomes favorable as the hydrogen partial pressure increases, and the unreacted ester is difficult to separate from alcohol, and thus additional purification and recovery are required.

PCT WO 2008/070561 discloses a process of preparing an alcohol mixture, comprising pretreating and fermenting biomass thus producing a carboxylate mixture or a carboxylic acid mixture which is then reacted with a high-molecular-weight alcohol to thus be converted into ester, and then performing hydrogenation. This process requires two-step catalytic processes in order to produce alcohol. For example, ammonium acetate is reacted with heptanol which is a high-molecular-weight alcohol, thus preparing acetic acid heptyl ester, which is then treated in a high-pressure hydrogen atmosphere, yielding ethanol and heptanol. This reaction is represented as below.

1 Step: ammonium acetate+heptanol→acetic acid heptyl ester+water+ammonia (esterification)
2 Step: acetic acid heptyl ester+hydrogen→ethanol+heptanol (hydrocracking)

This process should include an additional step for removing ammonia in addition to the step for the typical esterification. If the reaction takes place at a temperature range falling outside of an appropriate temperature range in a state of ammonia not having been completely removed, acetamide is formed as a by-product.

The above process converts carboxylic acid into the corresponding alcohol using the two-step reactions.

In order to simplify the two-step catalytic reactions, Korean Laid-open Patent Publication No. 2009-103720 discloses the use of both a carboxylic acid and an alcohol as reactants so that esterification and hydrogenation are simultaneously carried out in a reactor thereby simplifying the complicated process.

Also, Korean Laid-open Patent Publication No. 2009-0049656 discloses a method of preparing n-butanol using direct hydrogenation of butyric acid in the presence of a catalyst comprising a Cu based catalyst and a diluent such as silica, alumina, titania and zinc oxide. This patent is problematic because the amount of diluent relative to Cu is restricted.

The process of preparing alcohol from a carboxylic acid which is produced by fermenting biomass is known. In the process, the catalyst used to prepare alcohol from a carboxylic acid is mainly a commercially available Cu catalyst.

In the case of the commercially available Cu catalyst, its activity is undesirably low for a carboxylic acid having high acidity such as acetic acid.

The catalysts used to prepare ethanol from acetic acid are known to be Pt and Sn supported on silica as disclosed in US Patent Application No. 20100121114. U.S. Pat. No. 4,990,655 discloses a catalyst comprising a graphite carbon support and an active component composed of a Group 8 noble metal and Re in order to prepare ethanol or propanol from acetic acid or propionic acid.

The currently available catalysts are unsatisfactory when preparing alcohol from an acid mixture comprising two or more carboxylic acids including a carboxylic acid having high acidity such as acetic acid.

DISCLOSURE

Technical Problem

Accordingly, the present invention has been developed in light of the above problems occurring in the related art, and the present invention is intended to provide a method of preparing a nano-sized Cu based catalyst including dissolving, in an aqueous solution, a first component comprising a Cu precursor, a second component precursor comprising one or more selected from the group consisting of transition metals, alkaline earth metals and Group IIIb metals, and a third component precursor comprising one or more selected from the group consisting of alumina, silica, silica-alumina, magnesia, titania, zirconia and carbon and then stirring the resulting solution; precipitating the stirred mixture solution using $Na_2CO_3$ and NaOH to form a catalyst precursor precipitate; and washing and filtering the formed catalyst precursor precipitate.

Also the present invention is intended to provide a nano-sized Cu based catalyst, prepared using the above method.

Also the present invention is intended to provide a nano-sized Cu based catalyst, suitable for use in hydrogenation or dehydrogenation.

Also the present invention is intended to provide a method of preparing alcohol by reacting carboxylic acid and hydrogen using the hydrogenation catalyst.

The technical problem of the present invention is not limited thereto, and the other technical problems will be able to be apparently understood to those having ordinary skill from the following description.

Technical Solution

An aspect of the present invention provides a method of preparing a nano-sized copper based catalyst, comprising dissolving, in an aqueous solution, a first component comprising a Cu precursor, a second component precursor comprising one or more selected from the group consisting of a transition metal, an alkaline earth metal and a Group Mb metal, and a third component precursor comprising one or more selected from the group consisting of alumina, silica, silica-alumina, magnesia, titania, zirconia and carbon and then performing stirring thus obtaining a stored mixture solution; precipitating the stirred mixture solution using $Na_2CO_3$ and NaOH, thus forming a catalyst precursor precipitate; and washing and filtering the formed catalyst precursor precipitate.

Another aspect of the present invention provides a nano-sized Cu based catalyst, prepared using the above method.

A further aspect of the present invention provides a nano-sized Cu based catalyst suitable for use in hydrogenation, prepared using the above method.

Still a further aspect of the present invention provides a method of preparing alcohol, comprising reacting hydrogen with carboxylic acid comprising a single acid or an acid mixture of two or more acids derived from a microorganism fermented solution, using the hydrogenation catalyst.

Advantageous Effects

In a method of preparing a Cu based catalyst according to the present invention, Cu, a transition metal, an alkaline earth metal, a Group IIIb metal, alumina, silica, silica-alumina, magnesia, titania, zirconia, a carbon component, amounts of these components, the kind of precipitant, and the pH upon co-precipitation are adjusted, so that the nano-sized Cu based catalyst can be produced.

Also, the nano-sized Cu based catalyst according to the present invention is effective in the preparation of a single alcohol or an alcohol mixture from a single acid or an acid mixture.

MODE FOR INVENTION

Hereinafter, a detailed description will be given of the present invention.

According to an embodiment of the present invention, a method of preparing a Cu based catalyst includes dissolving, in an aqueous solution, a first component comprising a Cu precursor, a second component precursor comprising one or more selected from the group consisting of a transition metal, an alkaline earth metal and a Group Mb metal, and a third component precursor comprising one or more selected from the group consisting of alumina, silica, silica-alumina, magnesia, titania, zirconia and carbon and then stirring the resulting solution; precipitating the stored mixture solution using $Na_2CO_3$ and NaOH to form a catalyst precursor precipitate; and washing and filtering the formed catalyst precursor precipitate.

The specific tams used throughout the specification and claims are defined as follows.

As used herein, the term "Cu based catalyst" means that Cu acts as a main active catalyst. Even when it is Cu based, Cu which is essential need not be necessarily used in an amount larger than amounts of the other components of the catalyst.

The term "nano-sized" means a size ranging from 1 nanometer to hundreds of nanometers when the particle size is calculated using chemical adsorption-desorption of nitrous oxide ($N_2O$) gas and chemical adsorption-desorption of CO active gas or the Cu peak of XRD (X-ray diffraction patterns).

The term "Cu precursor" means a Cu salt, which may be present in the form of Cu or Cu oxide after burning.

The term "second component precursor" means a salt of a transition metal, an alkaline earth metal, a Group III metal or a mixture thereof, which may be present in the form of a transition metal, an alkaline earth metal, a Group III metal or an oxide thereof after burning.

Used as the first component of the Cu based catalyst according to the present invention, the Cu precursor may include a nitrate, an acetate, a chloride and so on. The copper nitrate hydrate is exemplified by $Cu(NO_3)_2 \cdot nH_2O$, for example, trihydrate, hexahydrate, nonahydrate, etc., and is well dissolved in water or ethanol.

Used as the second component of the Cu based catalyst according to the present invention, the transition metal, alkaline earth metal or Group IIIb metal is mixed with the Cu catalyst, and this component itself is active but its activity is lower than that of Cu. The transition metal which can be the component of the Cu based catalyst includes Zn, Co, Ni, Cr, Fe, Mo, Nb, Mn, Pt, Pd, Rh or Ru, and the alkaline earth metal includes Mg, Ca, Sr or Ba, and the Group IIIb metal includes Ga.

In the Cu based catalyst, the transition metal, alkaline earth metal, or Group IIIb metal need not necessarily be used in an amount less than that of Cu, and may be used in a larger amount than the Cu. Particularly useful is a molar ratio of Cu to the second component of 1:0.4-3.5.

In the Cu based catalyst according to the present invention, the third component may include alumina, silica, silica-alumina, magnesia, titania, zirconia, carbon or mixtures thereof. This component itself has no activity but is added in a small amount upon preparation of the catalyst so as to increase the activity, selectivity and stability of the main catalyst or to support the catalyst. Although the amount of this component is not particularly limited, the molar ratio of Cu to the second component to the third component of 1:0.8-1.5:0.2-0.5 is particularly useful.

A typical Cu based catalyst mainly includes Cu and Zn. Such a CuZn catalyst is poor in terms of Cu size, specific surface area, and dispersibility.

However, the present inventors have found the fact that when alumina is added to the CuZn catalyst, Cu dispersibility may be increased and Cu may be reduced at low temperature. For example, compared to the CuZn catalyst having Al added thereto, the catalyst having no Al is not completely converted into metal Cu upon reduction and large Cu particles are formed.

Furthermore, the present inventors have discovered the fact that the particle size of the Cu based catalyst is important because hydrogenation efficiency is determined thereby, and also that when Cu, a second component comprising a transition metal, alkaline earth metal, Group IIIb metal or a mixture thereof and a third component comprising alumina, silica, silica-alumina, magnesia, titania, zirconia, carbon or a mixture thereof are used, a Cu based catalyst having a size from 1 nm to 50 nm, and particularly a size of 20 nm or less, has hydrogen reduction properties that are effective.

When both the second component and the third component are used in the Cu based catalyst, hydrogen reduction properties become better. Furthermore, when the molar ratio of Cu is used in an amount smaller than the amount of the second component, the resulting catalyst may be reduced at lower temperature, thus increasing hydrogenation efficiency.

Thus, the hydrogen reducibility of the Cu based catalyst particles may be controlled by adjusting the ratio of Cu to the second component.

In the method of preparing the catalyst according to the embodiment of the present invention, the first step includes dissolving the first component precursor comprising the Cu precursor, the second component precursor comprising one or more selected from the group consisting of a transition metal, an alkaline earth metal and a Group IIIb metal, and the third component precursor comprising one or more selected from the group consisting of alumina, silica, silica-alumina, magnesia, titania, zirconia and carbon in the aqueous solution, and then performing stirring thus obtaining the mixture solution. The aqueous solution includes pure water but is not limited thereto. The size of the Cu based catalyst affects hydrogenation efficiency as mentioned above, and the catalyst size varies depending on the molar ratio of Cu to the second component.

The second step includes precipitating the mixture solution obtained in the first step using a precipitant, thus forming the catalyst precursor precipitate.

$Na_2CO_3$ and NaOH are sequentially used as precipitants, so that the catalyst precursor precipitate is formed. In this case, Cu metal particles having a smaller size may be obtained compared to when using either $Na_2CO_3$ or NaOH as the precipitant.

In the case where NaOH is used as the precipitant Cu, the second component precursor and the third component precursor may be rapidly precipitated and thus the metal particles are non-uniformly mixed in the course of precipitation On the other hand, in the case where $NH_3$ aqueous solution is used as the precipitant, the pH does not stay uniform throughout co-precipitation and aging. Hence, in the course of preparing the catalyst, Cu, the second component precursor and the third component precursor are non-uniformly structured, and the size of Cu particles is not decreased as desired due to changes in the pH.

However, if the pH is gradually increased using $Na_2CO_3$ and then further increased using NaOH the Cu, the second component and the third component can be prevented from rapidly precipitating, prohibiting the metal particles from being non-uniformly mixed, and also maintaining the pH uniform to obtain the Cu based catalyst having uniform nanoparticles.

In the precipitation step, the pH may fall in the range of 5.0-11.0.

The initial catalyst precursor mixture comprising the Cu precursor, the second component precursor and the third component precursor which are dissolved in the aqueous solution has a pH of 2-4. When an alkaline precipitant is slowly added thereto, the catalyst precursor begins to be precipitated starting at a pH of 5.

As the amount of alkaline precipitant is increased, the color of the metal mixture solution becomes darker, and the nano-sized Cu based catalyst is precipitated until the pH of 9. The re-dissolution of the precipitated metal in the aqueous solution may occur when the pH is higher than 9. Thus, in the precipitation step, co-precipitation is performed at a pH of 5.0-11.0, and particularly a pH of 6-9.

In the third step, the catalyst precursor precipitate is washed and then filtered in order to make it neutral.

In the case where the Cu based catalyst is used for hydrogenation, the final metal catalyst is obtained in the third step, after which the prepared metal catalyst is dried and then burned so as to be converted into metal oxide and thus used.

According to an embodiment of the present invention, a nano-sized Cu based catalyst obtained using the above preparation method is provided, and particularly a Cu based catalyst having a size of 20 nm or less is provided.

The nano-sized Cu based catalyst obtained using the preparation method according to the embodiment of the present invention may be used for hydrogenation or dehydrogenation.

The nano-sized Cu based catalyst according to the present invention may be used for a water-gas shift reaction, methanol reforming for producing hydrogen from methanol, $CO_2$ hydrogenation for synthesizing methanol from hydrogen and $CO_2$, hydro-dechlorination for removing Cl from Cl-containing hydrocarbon, or production of γ-butyrolactone from 1,4-butanediol (1,4-BDO).

The Cu based metal particles used for hydrogenation or dehydrogenation may have a size of 20 nm or less.

For example, butyric acid is directly hydrogenated using a catalyst comprising Cu, Zn as the second component, and alumina as the third component, thus preparing butanol. In this case, the butyric acid conversion and the butanol selectivity increase linearly in proportion to the decrease in the molar ratio of Cu of the Cu based metal, which coincides with the trend in which the size of Cu particles of the Cu based catalyst is decreased. When reducibility increases in the low temperature range, the catalyst is highly active in the direct hydrogenation of butyric acid. The butyric acid conversion and the butanol yield in the presence of the Cu based catalyst are the greatest when the Cu particles of the Cu based catalyst have a size of 20 nm or less as shown in Table 1 and FIG. 2.

According to an embodiment of the present invention, there is provided a method of preparing alcohol by reacting hydrogen with carboxylic acid comprising a single acid or an acid mixture of two or more acids derived from a microorganism fermented solution, using the nano-sized Cu based catalyst prepared by the method of present invention.

According to a specific embodiment, the acid mixture may be a mixture comprising two or more carboxylic acids selected from among C2-C7 carboxylic acids. The source of the carboxylic acid according to the present invention is not particularly limited. According to a specific embodiment, the carboxylic acid may be derived from biomass, and according to another specific embodiment, the carboxylic acid may be derived from a microorganism fermented solution.

In the present invention, the preparation of alcohol by reacting carboxylic acid with hydrogen using the hydrogenation catalyst is simpler compared to conventional complicated two-step processes comprising esterifying carboxylic acid in the presence of an acid catalyst thus producing a carboxyl ester and then hydrocracking the carboxyl ester under high pressure, thus obtaining the corresponding alcohol. Furthermore, this alcohol preparation is different from one-step process using both carboxylic acid and alcohol as reactants.

Because metal is typically dissolved well in an acid, the metal catalyst may be dissolved in an acid in a liquid phase. In the case where a carboxylic acid is used as a reactant, it should be sufficiently gasified so that the reactant is not present in a liquid phase, and the contact time with the catalyst should be short. In the case where a carboxylic acid is used as the reactant, almost all of the metal catalysts are known to use a noble metal catalyst which is stable in an acid.

Typically organic acids produced from biomass include large amounts of C2 (acetic acid), C3 (propionic acid), C4 (butyric acid), C5 (pentanoic acid), C6 (hexanoic acid), C7 (heptanoic acid), etc.

In the esterification of a carboxylic acid in conventional two-step processes that prepare alcohol from a carboxylic acid, esterification activity may decrease due to steric hindrance in proportion to an increase in the number of carbons.

However, in direct hydrogenation, lower activity (acid strength: acetic acid>propionic acid>butyric acid>pentanoic acid>hexanoic acid>heptanoic acid) has been found to be true in proportion to the decrease in the number of carbons. This is considered to be because the acid strength of carboxylic acid causes the catalyst to be inactivated. Even when a hydrogenation catalyst usable for preparing alcohol from an acid having low acid strength is applied, it is difficult to make an alcohol from an acid having high acid strength. In particular, acetic acid is stronger than the acid strength of other organic acids, and may undesirably deteriorate the activity of catalyst.

Because acetic acid has acid strength higher than other acids, if a feed is not completely converted into alcohol under strong acid conditions, the metal is dissolved, undesirably decreasing the activity of the catalyst. When the catalyst which is efficient at converting butyric acid which has a lower acid strength than acetic acid into butanol using direct hydrogenation is used to convert acetic acid into ethanol, its activity may deteriorate.

However, the catalyst according to the present invention may be used for the direct hydrogenation of an acid mixture including strong acetic acid, other than the single acid, thus efficiently preparing an alcohol mixture.

In the method of preparing alcohol by reacting carboxylic acid with hydrogen according to the present invention, the hydrogen flow rate and pressure are favorably higher. If the hydrogen flow rate is low, relatively high pressure is required. According to a specific embodiment, the hydrogen flow rate is 1-100 times that of carboxylic acid based on the molar ratio, and the hydrogen pressure ranges from atmospheric pressure to 100 bar.

In the present invention, the reaction temperature is not particularly limited, and may vary depending on the kind of carboxylic acid. If the temperature is low, the carboxylic acid which is the reactant is not sufficiently gasified but is partially present in a liquid phase and thus may dissolve the metal component of the catalyst.

According to a specific embodiment, when an acid mixture comprising acetic acid and butyric acid is used as a feed for direct hydrogenation, it should be sufficiently gasified taking into consideration the boiling point of acetic acid of 118° C. and the boiling point of butyric acid of 164° C.

Even when a carboxylic acid having a high boiling point, for example, a carboxylic acid having a large number of carbons, is used as the reactant, it does not mean that the reaction should be performed at a temperature higher than the boiling point. In the case of acetic acid, the reaction temperature should be higher compared to when using butyric acid and also more energy is required to activate the carbonyl group present in carboxylic acid, regardless of boiling point.

According to a specific embodiment, the temperature appropriate for direct hydrogenation of acetic acid is higher than that of the direct hydrogenation of butyric acid, and the temperature adapted for direct hydrogenation of a carboxylic acid mixture comprising acetic acid and butyric acid is 200-350° C., and particularly 280-320° C.

According to a specific embodiment, the hydrogen flow rate used in the alcohol preparation method according to the present invention is 1-100 times that of the carboxylic acid based on the molar ratio, and the hydrogen pressure falls in the range of from atmospheric pressure to 100 bar.

The hydrogenation catalyst according to the present invention is not limited to a special component ratio of the acid mixture derived from biomass.

In the case of carboxylic acid derived from microorganisms, acetic acid is mainly produced. Acids other than acetic acid may be produced depending on the fermentation conditions. In this case, acetic acid is essentially produced. Thus, when alcohol is prepared by hydrogenating the acid mixture derived from microorganisms, a catalyst effective for hydrogenating strong acetic acid must be used.

According to a specific embodiment, the hydrogenation catalyst according to the present invention is effective when the ratio of acetic acid to other carboxylic acids is 1.0-9.0:1.0 in the feed comprising the mixture comprising carboxylic acids derived from microorganisms.

According to a specific embodiment, when the catalyst comprising Cu, Zn as the second component and alumina as the third component is used, butyric acid and acetic acid are directly hydrogenated thus preparing butanol and ethanol. In this case, as the molar ratio of the Cu of the catalyst decreases, the conversion of butyric acid and acetic acid and the selectivity of butanol and ethanol linearly increase. This coincides with the trend in which the size of Cu particles of the catalyst is decreased, and as reducibility increases in the low temperature range, this catalyst is highly active in the direct hydrogenation of the acid mixture comprising acetic acid and butyric acid.

Below, the catalyst preparation method according to the present invention is described through the following examples and comparative examples.

Comparative Example 1

Preparation of CuZn Catalyst

In order to prepare a CuZn catalyst (Cu:Zn molar ratio= 8:2, which is referred to as "CZ-82 catalyst"), 24.8 g of copper nitrate [$Cu(NO_3)_2 \cdot 3H_2O$] and 7.93 g of zinc nitrate [$Zn(NO_3)_2 \cdot 6H_2O$] were dissolved in 300 ml of ultrapure distilled water (a resistance of 18 MΩ or more) and then stirred for 1 hour.

The stirred catalyst precursor mixture solution had a pH of 1.0-3.0, after which 1.0 M $Na_2CO_3$ was slowly added to the catalyst precursor mixture solution at a rate of 1.0 cc/min so as to attain a pH of 4.0-5.0, and then 1.0 M NaOH solution was added in droplets thereto at a rate of 1.0 cc/min until the pH of 7.0, so that the catalyst precursor was precipitated from the aqueous solution.

The precipitated metal mixture was stirred at 25° C. for 24 hours and then allowed to stand for 6 hours so that water and catalyst precursor were sufficiently phase separated, thus forming a catalyst precursor precipitate which was then sufficiently washed and filtered until the pH of 7.0, yielding a final metal catalyst. The prepared metal catalyst was sufficiently dried at 100° C. for 24 hours and then burned for 3 hours under flowing air at 450° C. and thus converted into metal oxide.

Example 1

Preparation of CuZnAl Catalyst (Effect of Addition of Al)

In order to evaluate changes in the activity of the catalyst when adding Al to the CZ-82 catalyst of Comparative Example 1, a CuZnAl catalyst (Cu:Zn:Al molar ratio=8:1:1, which is referred to as "CZA-811 catalyst") was prepared. Specifically, 24.8 g of copper nitrate [$Cu(NO_3)_2 \cdot 3H_2O$], 3.96 g of zinc nitrate [$Zn(NO_3)_2 \cdot 6H_2O$] and 5.0 g of aluminum nitrate [$Al(NO_3)_2 \cdot 6H_2O$] were dissolved together in 300 ml of ultrapure distilled water and then stirred for 1 hour. Thereafter, 1.0 M $Na_2CO_3$ was slowly added to the catalyst precursor mixture solution at a rate of 1.0 cc/min until a pH of 4.0-5.0 and then 1.0 M NaOH solution was added in droplets thereto at a rate of 1.0 cc/min until the pH of 7.0, so that the catalyst precursor was precipitated from the aqueous solution.

The precipitated metal was washed, filtered and dried as in Comparative Example 1, and then burned for 3 hours under flowing air at 450° C.

In the CuZnAl catalyst system, in order to evaluate the activity of the catalyst depending on changes in the Cu/Zn molar ratio, the amount of alumina was fixed, and the ratio of Cu and Zn was changed, thus preparing CuZnAl catalysts.

Example 2

Preparation of Catalyst Having Molar Ratio of Cu to Zn to Al of 7:2:1

In order to prepare a CuZnAl catalyst having a molar ratio of Cu to Zn to Al of 7:2:1 (which is referred to as "CZA-721"), 21.7 g of copper nitrate [$Cu(NO_3)_2 \cdot 3H_2O$], 7.9 g of zinc nitrate [$Zn(NO_3)_2 \cdot 6H_2O$] and 5.0 g of aluminum nitrate [$Al(NO_3)_2 \cdot 6H_2O$] were dissolved together in 300 ml of ultrapure distilled water and then stirred for 1 hour, after which the subsequent procedures were performed in the same manner as in Comparative Example 1, thereby preparing the catalyst.

Example 3

Preparation of Catalyst Having Molar Ratio of Cu to Zn to Al of 6:3:1

In order to prepare a CuZnAl catalyst having a molar ratio of Cu to Zn to Al of 6:3:1 (which is referred to as "CZA-631"), 18.6 g of copper nitrate [$Cu(NO_3)_2 \cdot 3H_2O$], 11.9 g of zinc nitrate [$Zn(NO_3)_2 \cdot 6H_2O$] and 5.0 g of aluminum nitrate [$Al(NO_3)_2 \cdot 6H_2O$] were dissolved together in 300 ml of ultrapure distilled water and then stirred for 1 hour, after which the subsequent procedures were performed in the same manner as in Comparative Example 1, thereby preparing the catalyst.

Example 4

Preparation of Catalyst Having Molar Ratio of Cu to Zn to Al of 5:4:1

In order to prepare a CuZnAl catalyst having a molar ratio of Cu to Zn to Al of 5:4:1 (which is referred to as "CZA-541"), 15.5 g of copper nitrate [Cu(NO$_3$)$_2$·3H$_2$O], 15.9 g of zinc nitrate [Zn(NO$_3$)$_2$·6H$_2$O] and 5.0 g of aluminum nitrate [Al(NO$_3$)$_2$·6H$_2$O] were dissolved together in 300 ml of ultrapure distilled water and then stirred for 1 hour, after which the subsequent procedures were performed in the same manner as in Comparative Example 1, thereby preparing the catalyst.

Example 5

Preparation of Catalyst Having Molar Ratio of Cu to Zn to Al of 4:5:1

In order to prepare a CuZnAl catalyst having a molar ratio of Cu to Zn to Al of 4:5:1 (which is referred to as "CZA-451"), 12.4 g of copper nitrate [Cu(NO$_3$)$_2$·3H$_2$O], 19.8 g of zinc nitrate [Zn(NO$_3$)$_2$·6H$_2$O] and 5.0 g of aluminum nitrate [Al(NO$_3$)$_2$·6H$_2$O] were dissolved together in 300 ml of ultrapure distilled water and then stirred for 1 hour, after which the subsequent procedures were performed in the same manner as in Comparative Example 1, thereby preparing the catalyst.

Example 6

Use of Na$_2$CO$_3$ and then NaOH as Precipitant

In order to evaluate changes in activity of the catalyst depending on the kind of precipitant in a CuZnAl catalyst system, Na$_2$CO$_3$ and then NaOH were sequentially used as precipitants to prepare a catalyst. This catalyst is the CZA-631 catalyst of Example 3 among the CZA catalysts having different molar ratios of Cu/Zn. These precipitants each were prepared in a concentration of 1.0 M. Specifically, 18.6 g of copper nitrate [Cu(NO$_3$)$_2$·3H$_2$O], 11.9 g of zinc nitrate [Zn(NO$_3$)$_2$·6H$_2$O] and 5.0 g of aluminum nitrate [Al(NO$_3$)$_2$·6H$_2$O] were dissolved together in 300 ml of ultrapure distilled water, and then stirred for 1 hour.

1.0 M Na$_2$CO$_3$ was slowly added thereto at a rate of 1.0 cc/min until a pH of 4.0-5.0 and then 1.0 M NaOH solution was added in droplets thereto at a rate of 1.0 cc/min until the pH of 7.0, so that the catalyst precursor was precipitated from the aqueous solution The subsequent procedures were performed in the same manner as in Comparative Example 1.

Example 7

Co-Precipitation of CZA-631 Catalyst at pH of 8.0

This example was performed in the same manner as in Example 3, with the exception that, upon co-precipitation, after use of the Na$_2$CO$_3$ precipitant, NaOH was added at a rate of 1.0 cc/min so that the pH was 8.0 instead of 7.0.

Example 8

Co-Precipitation of CZA-631 Catalyst at pH of 9.0

This example was performed in the same manner as in Example 3, with the exception that, upon co-precipitation, after use of the Na$_2$CO$_3$ precipitant NaOH was added at a rate of 1.0 cc/min so that the pH was 9.0 instead of 7.0.

Comparative Example 2

Use of NaOH as Precipitant

This example was performed in the same manner as in Example 6, with the exception that NaOH serving as a precipitant was added in droplets at a rate of 1.0 cc/min until the pH of 7.0, instead of using Na$_2$CO$_3$ and then NaOH as precipitants, whereby the catalyst precursor was precipitated from the aqueous solution.

Comparative Example 3

Use of NH$_3$ Aqueous Solution as Precipitant

This example was performed in the same manner as in Example 6, with the exception that a NH$_3$ aqueous solution (28-30 wt %) serving as a precipitant was added in droplets at a rate of 1.0 cc/min until the pH of 7.0, instead of using Na$_2$CO$_3$ and then NaOH as precipitants, whereby the catalyst precursor was precipitated from the aqueous solution.

Test Example 1

Particle Size, Specific Surface Area and Dispersibility of Metal Cu of Cu Based Catalyst The Cu particle size, specific surface area and dispersibility of the CuZn catalyst and the CuZnAl-811, CuZnAl-721, CuZnAl-631, CuZnAl-541 and CuZnAl-451 catalysts were determined by reducing the Cu based catalyst at 300° C. for 2 hours, adsorbing N$_2$O gas at 90° C., and then calculating the amount of N$_2$ desorbed after heated.

Table 1 below shows the Cu particle size, specific surface area and dispersibility of the catalysts. The Cu particle size, specific surface area and dispersibility of the CuZn catalyst were not measured unlike the CuZnAl catalysts. This is considered to be because Al functions to increase the dispersibility of Cu and causes Cu to be reduced at low temperature upon preparation of the CuZnAl catalyst. The catalyst having no Al was not sufficiently converted into metal Cu upon reduction, and the Cu particles that were formed were so large that they exceeded the measurement range.

TABLE 1

|  | Cu Particle Size (nm) | Cu Specific Surface Area (m$^2$/g) | Dispersibility (%) |
| --- | --- | --- | --- |
| CZ-82 Cu:Zn = 8:2 | 500 nm or more | 1.0 or less | 1.0% or less |
| CZA-811 Cu:Zn:Al = 8:1:1 | 62 | 11 | 1.7 |
| CZA-721 Cu:Zn:Al = 7:2:1 | 35 | 20 | 3.0 |
| CZA-631 Cu:Zn:Al = 6:3:1 | 28 | 24 | 3.7 |
| CZA-541 Cu:Zn:Al = 5:4:1 | 20 | 33 | 5.2 |
| CZA-451 Cu:Zn:Al = 4:5:1 | 16 | 42 | 6.6 |

The size of Cu particles was observed depending on the molar ratio of Cu to Zn under conditions of a fixed Al content. Consequently, as the Cu content is comparatively lower, the Cu particle size linearly decreases whereas the specific surface area and the dispersibility of Cu are comparatively increased.

Unlike the catalyst composed exclusively of Cu and Zn, the CZA catalyst was formed so that the Cu particle size was about 70 nm or less. Furthermore, the size of Cu particles was decreased in proportion to the decrease in the molar ratio of Cu/Zn In the case of CZA-541 catalyst, the Cu particles having a size of about 20 nm or less were formed.

Test Example 2

Hydrogen Reduction Properties of Commercially Available Cu Based Catalyst

Figure 1:
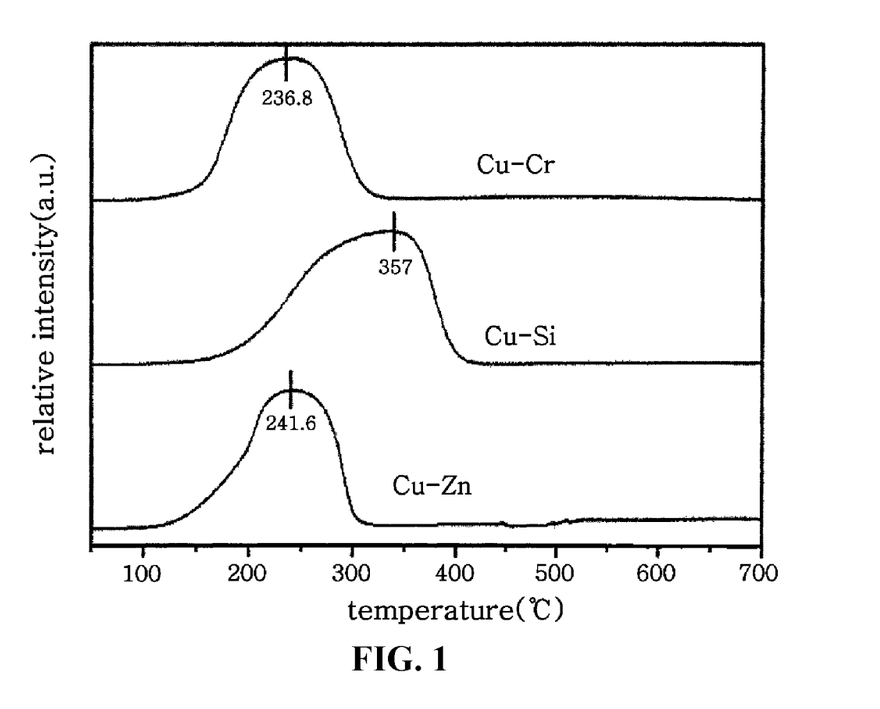
FIG. 1 shows the hydrogen reduction properties of Cu based catalysts.

The hydrogen reduction properties of Cu—Cr, Cu—Si and Cu—Zn as Cu based catalysts were evaluated. The results are shown in FIG. 1. In order to evaluate the hydrogen reduction properties, TPR (Temperature Programmed Reduction) analysis was conducted. The Cu catalyst was pretreated at 120° C. at a rate of 50 cc/min in a He atmosphere for 1 hour, cooled to room temperature, and then heated to 700° C. in a hydrogen atmosphere, after which the reducibility of the catalyst was measured.

In the results, the Cu—Cr catalyst having reduced Cu particles the size of which was the smallest was reduced at the lowest temperature, and the Cu—Si catalyst including only the dispersant was reduced at the highest temperature.

Test Example 3

Figure 2:
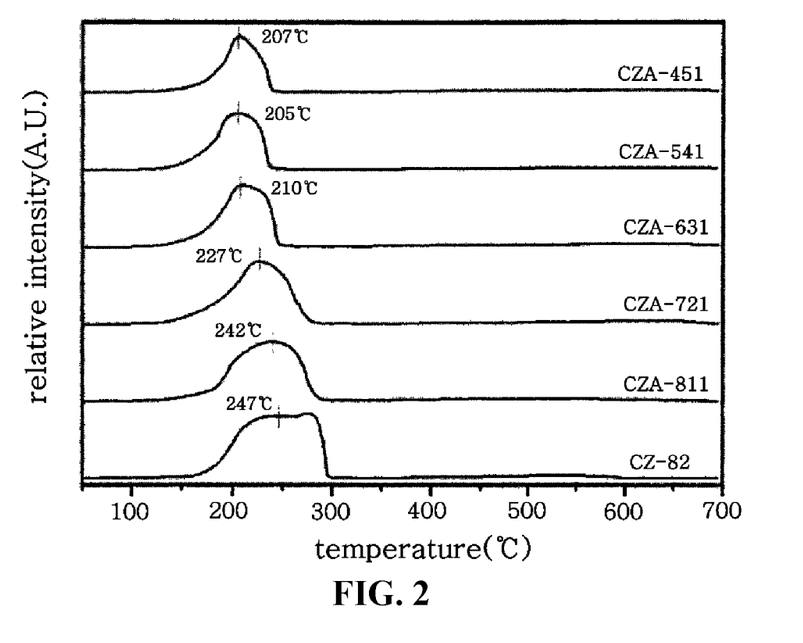
FIG. 2 shows the hydrogen reduction properties of the catalysts depending on the ratio of Cu, Zn and Al.

Hydrogen Reduction Properties of Cu Based Catalyst Depending on Cu/Zn Ratio The hydrogen reduction properties of the CZ catalyst and the CZA catalysts were measured using TPR (Temperature Programmed Reduction). The Cu catalyst was pretreated at 120° C. at a rate of 50 cc/min in a He atmosphere for 1 hour, cooled to room temperature, and then heated to 700° C. in a hydrogen atmosphere, after which the reducibility of the catalyst was measured. FIG. 2 shows the hydrogen reduction properties of the CZ catalyst and the CZA catalysts. When observing the temperature positions of the reduction peaks, the CZ catalyst was reduced at the temperature higher than were the CZA catalysts.

In the CZA based catalysts, as the ratio of Cu/Zn decreases, the CZA catalyst is reduced at lower temperature, which coincides with the trend as in Example 1 in which the size of Cu metal particles is decreased in proportion to the decrease in the molar ratio of Cu/Zn. Consequently, the reduction temperature of the CZA catalyst is lowered in proportion to the decrease in the size of the Cu metal particles, and the hydrogen reducibility of the Cu metal of the Cu particles can be controlled by adjusting the ratio of Cu/Zn.

Test Example 4

Direct Hydrogenation of Butyric Acid by Cu Based Catalyst

Figure 3:
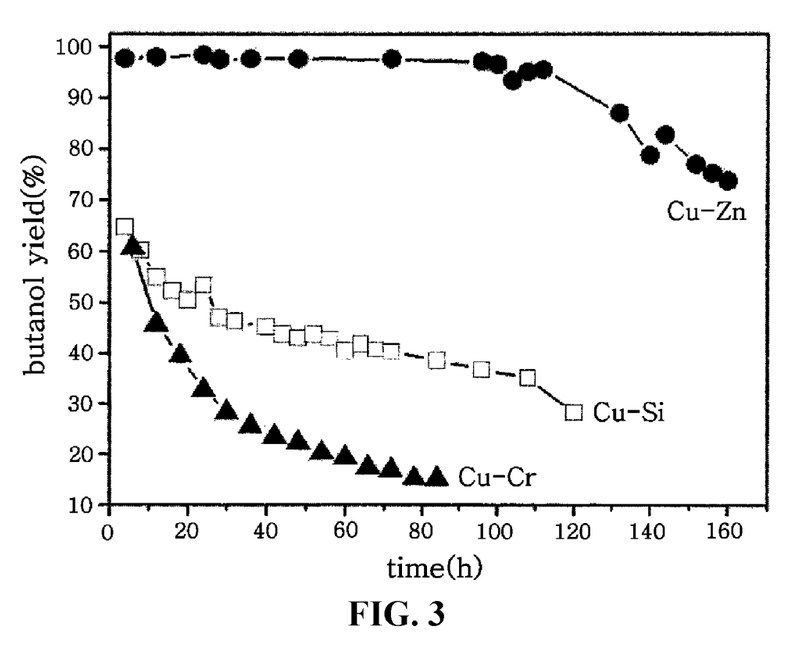
FIG. 3 shows the results of the direct hydrogenation of butyric acid using the Cu based catalysts.

FIG. 3 shows the results of applying the commercially available Cu catalysts to the direct hydrogenation of butyric acid which is a kind of carboxylic acid. The catalytic reaction was carried out at a reaction temperature of 270° C. and a reaction pressure of 550 psi under conditions of LHSV=0.9, and catalytic performance was thus evaluated.

Compared to the Cu—Cr catalyst which is considered to have superior catalytic performance resulting from improving hydrogen reduction properties in proportion to a decrease in the size of metal particles like typical hydrogenation, the Cu—Zn based catalyst had unexpectedly superior performance. The activity of the Cu—Cr catalyst was lower than that of the Cu—Si catalyst having only the dispersant without the co-catalyst component.

Meanwhile, the size of the Cu metal particles of the Cu—Si based catalyst, for example, a commercially available Cu—$SiO_2$ catalyst (CuO: 76, $SiO_2$, $Cr_2O_3$: 1.5, MgO: 3, graphite) was measured to be 184 nm. The performance of the commercially available Cu—$SiO_2$ catalyst was measured at a reaction temperature of 270° C. and a reaction pressure of 550 psi under operating conditions of LHSV=0.9, and consequently the butanol selectivity was 31.9% and the butanol yield was 21.7%. Hence, when the above catalyst is applied to direct hydrogenation of acetic acid, it is expected to exhibit low ethanol selectivity and low ethanol yield.

Therefore, in direction hydrogenation of carboxylic acid, Zn could be expected to be more favorable than Cr as the co-catalyst component for activating Cu metal, in addition to the size of metal particles.

Test Example 5

Figure 4:
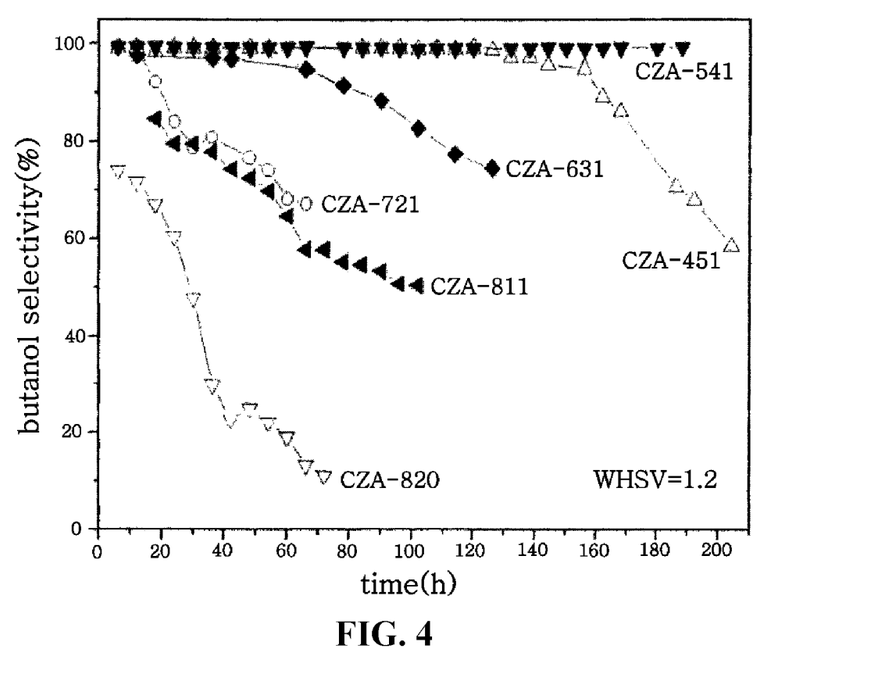
FIG. 4 shows the results of the direct hydrogenation of butyric acid depending on the ratio of Cu, Zn and Al.

Direct Hydrogenation of Butyric Acid by CZ and CZA Catalysts at Different Cu/Zn Molar Ratios The prepared catalysts were applied to direct hydrogenation of butyric acid. FIG. 4 shows the results of the direct hydrogenation of butyric acid by the Cu based catalysts according to the present invention having different compositions.

The activities of the prepared catalysts were tested using a continuous flow reactor having a fixed catalyst bed, and all the catalysts were reduction pretreated at 300° C. for 2 hours under a flow of hydrogen at 20 cc/min and a flow of nitrogen at 400 cc/min and then treated under a flow of hydrogen at 400 cc/min at 270° C. and 550 psi. Also, the ca alytic reaction was performed in such a manner that a feed was supplied into the reactor under conditions of WHSV=1.2, and an additional pre-heating zone was provided in the reaction introduction part so that butyric acid was sufficiently gasified in order to prevent it from being supplied in the form of a liquid phase to the catalyst.

The CZ-82 catalyst having no alumina had large metal particles and a small active area and thus resulted in low butyric acid conversion and drastically inactivated catalytic performance. On the other hand, in the case of the catalysts having alumina, the size of Cu particles was comparatively smaller, and the specific surface area of Cu was larger, resulting in increased butyric acid conversion and butanol selectivity. This is considered to be because alumina functions as a dispersant which increases the specific surface area of Cu metal. In the case of the CZA catalysts, the butyric acid conversion and the butanol selectivity linearly increased in proportion to the decrease in the molar ratio, which coincides with the trend in which the size of Cu particles of the CZA catalyst is decreased. As the reducibility of the catalyst in the low temperature range was increased, the activity thereof in the direct hydrogenation of butyric acid was increased.

The CZA-541 catalyst and the CZA-451 catalyst both having a Cu particle size of 20 nm or less exhibited butyric acid conversion and butanol yield superior to those of the other CZA catalysts. Compared to the CZA-451 catalyst having the relatively smaller particle size, the CZA-541 catalyst having larger particle size but relatively higher Cu content could be better in terms of durability.

In the direct hydrogenation of butyric acid, the catalyst should actively increase the activation of the carbonyl group present in the butyric acid. Upon activation of the carbonyl group, high hydrogen reduction properties of Cu importantly affect the ca alytic activity, in addition to the metal Cu size.

Thus, the CZA-541 catalyst, which has higher Cu content than that of the CZA-451 catalyst, is considered to have the Cu, Zn, Al structure with superior durability to butyric acid. When a catalyst having Cu particles that are small on the scale of ones of nm by decreasing Cu content was prepared and tested, the size of Cu particles in the catalyst was successfully decreased, but the ability of the catalyst to activate the carbonyl group in the butyric acid was diminished, undesirably deteriorating ca alytic performance in the direct hydrogenation of butyric acid.

Test Example 6

Figure 5:
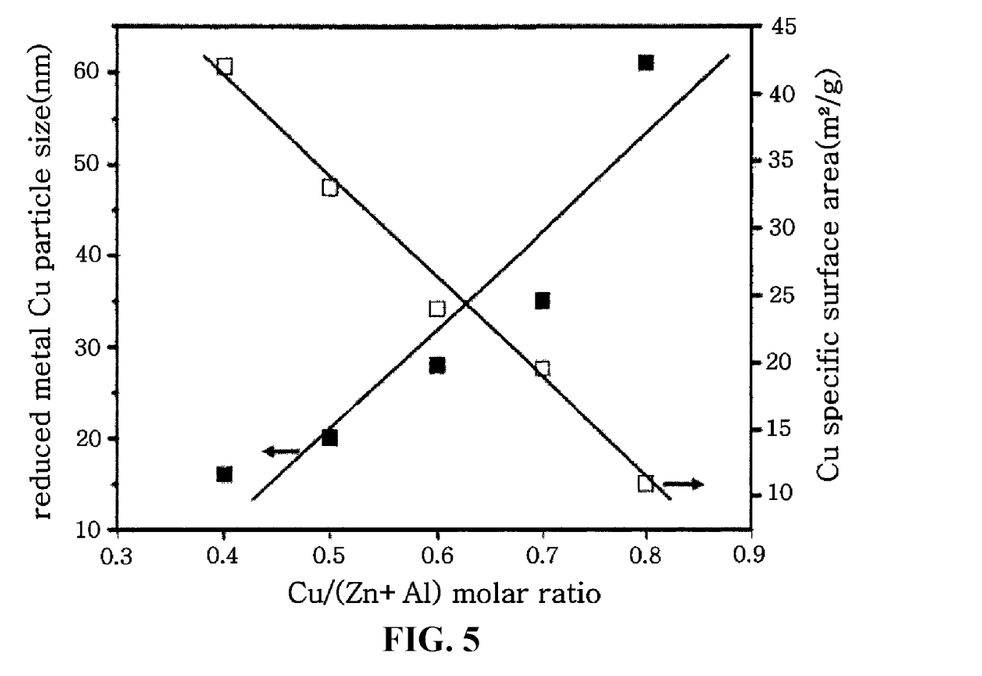
FIG. 5 shows the relation between the Cu particle size and the specific surface area depending on the ratio of Cu, Zn and Al.

Relation Between Cu Particle Size and Specific Surface Area Depending on Composition Ratio of Cu Based Catalyst The physical properties of six kinds of catalysts of Examples 1-5 are shown in FIG. 5. When the amount of Al was fixed to 10% in the total molar ratio and the ratio of Cu and Zn was changed, the particle size and specific surface area of the reduced Cu were measured. The results showed that as the ratio of Zn/Cu decreased, the size of reduced Cu particles linearly decreased and the specific surface area increased.

Test Example 7

Butanol Yield Depending on Cu Particle Size and Hydrogen Reduction Properties

Figure 6:
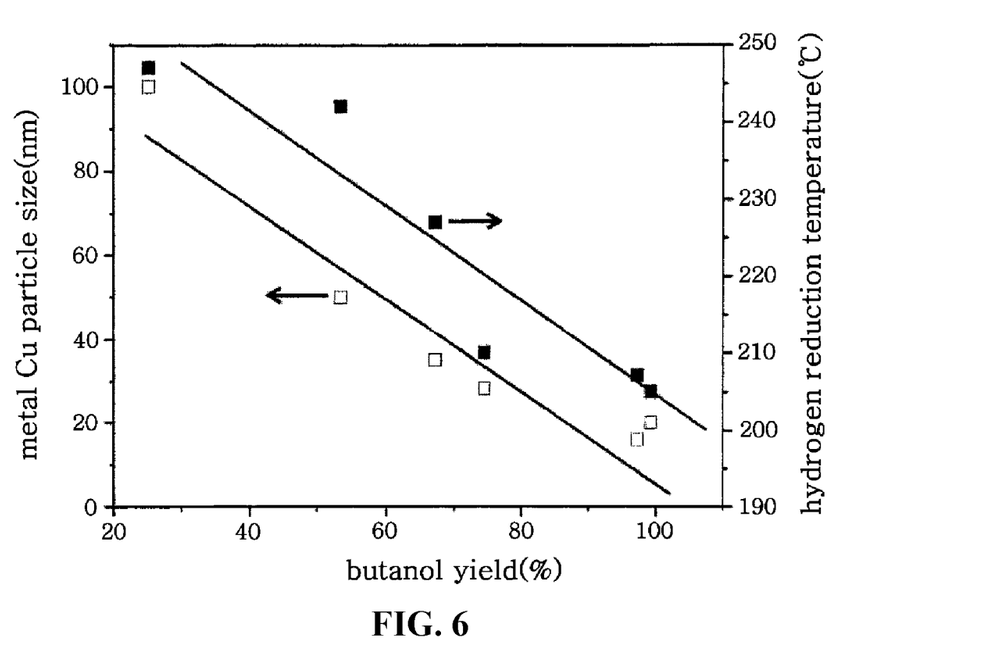
FIG. 6 shows the butanol yield depending on the Cu particle size and the hydrogen reduction temperature.

The catalysts of Examples 1-5 were applied to the direct hydrogenation of butyric acid. The results are shown in FIG. 6. The performances of all of the catalysts were evaluated at a reaction temperature of 270° C. and a reaction pressure of 550 psi under conditions of WHSV=1.2. Consequently, as the size of reduced Cu particles became smaller, the butanol yield was increased.

Furthermore, the use of the catalyst having superior hydrogen reduction properties, namely high reducibility at low temperature resulted in increased butanol yield.

In the direct hydrogenation of carboxylic acid, the reduced Cu particle size affected the hydrogen reduction properties, which was directly related to the hydrogenation.

Test Example 8

Changes in Particle Size of Cu Based Catalyst Depending on Kind of Precipitant

Upon preparation of the CZA-631 catalyst, a variety of precipitants were used, and the resulting catalysts were then applied to direct hydrogenation of butyric acid. The results are shown in Table 2 below. The catalytic reaction conditions were the same as those in Test Example 3 with the exception of WHSV=1.2. When 1.0 M NaOH and 1.0 M $NH_3$ aqueous solution were separately used as the precipitant, the particle size of Cu metal of the resulting catalysts was 100 nm or more. In addition, when 1.0 M $Na_2CO_3$ and 1.0 M NaOH were used together, the metal Cu particles of the resulting catalyst were highly dispersed on the scale of 20 nm or less.

This is considered to be because the Cu, Zn and Al precursors are uniformly structured upon precipitation. Unlike this, when 1.0 M NaOH was used as the precipitant, Cu, Zn, Al metals were rapidly precipitated, and thus metal particles were non-uniformly mixed. Also, when $NH_3$ aqueous solution was used as the precipitant, the pH was not kept uniform throughout co-precipitation and aging.

Hence, the small Cu particles were not formed in this preparation procedure because of the formation of the non-uniform structure of Cu, Zn and Al and changes in the pH. Thereby, when NaOH and $NH_3$ aqueous solution were separately used as the precipitant, the butanol yield resulting from direct hydrogenation of butyric acid was low.

TABLE 2

| Catalyst | Precipitant | pH upon Co-precipitation | Metal Particle Size (nm) | Butanol Yield (%) |
| --- | --- | --- | --- | --- |
| CZA-631 | NaOH, 1.0M | 7.0 | 207 | 71 |
| CZA-631 | $NH_3$ Aqueous Solution, 1.0M | 7.0 | 306 | 65 |
| CZA-631 | $Na_2CO_3$, 1.0M NaOH, 1.0M | 7.0 | 49 | 98 |

Test Example 9

Changes in Particle Size of Cu Based Catalyst Depending on the pH Upon Precipitation The CZA-631 catalysts were prepared at different pH values upon precipitation The results are shown in Table 3 below. The prepared catalysts were reacted under the same conditions as in Example 3. In the case of the catalyst precipitated under conditions of pH=9.0, high catalytic activity could be achieved. The pH of the metal precursor upon co-precipitation is known to importantly affect the formation of a uniform structure by interconnecting the metal components. In the catalysts prepared under pH conditions exceeding 9.0, the precipitated precursor was dissociated again in the aqueous solution in proportion to the increase in pH, and the amount of final catalyst was comparatively low.

TABLE 3

| Catalyst | Precipitant | pH upon Co-precipitation | Metal Particle Size (nm) | Butanol Yield (%) |
| --- | --- | --- | --- | --- |
| CZA-631 | $Na_2CO_3$, 1.0M NaOH, 1.0M | 7.0 | 48 | 75 |
| CZA-631 | $Na_2CO_3$, 1.0M NaOH, 1.0M | 8.0 | 38 | 81 |
| CZA-631 | $Na_2CO_3$, 1.0M NaOH, 1.0M | 9.0 | 29 | 95 |

Test Example 10

Butanol Yield and Butyric Acid Conversion Depending on Changes in Temperature

Figure 7:
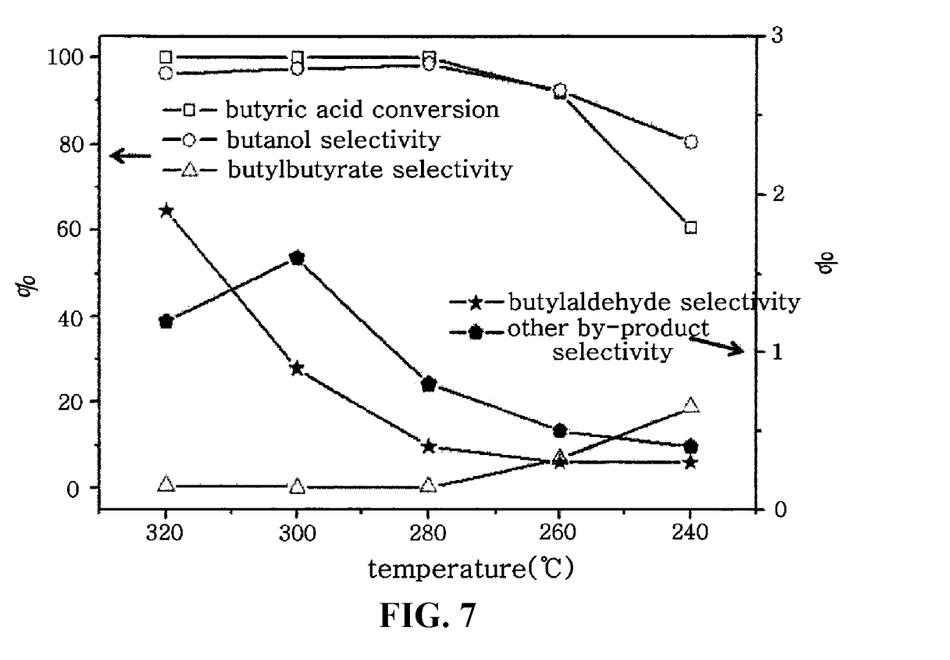
FIG. 7 shows the butanol yield and the butyric acid conversion depending on changes in temperature.

FIG. 7 shows the results of applying the CZA-541 catalyst of Example 4 to the direct hydrogenation of butyric acid in the temperature range decreased from 320° C. to 240° C. All reactions were performed under the conditions of a reaction pressure of 550 psi, butyric acid/hydrogen=57.0, WHSV=0.90.

At 320° C., the yield of butyl aldehyde which is a by-product of the direct hydrogenation of butyric acid was about 2%, and the butanol selectivity was about 97% or higher. At 280° C., the maximum butanol yield of 98.6% or higher was observed. For the reaction temperature range of 260° C. or lower, the butyric acid conversion was decreased. Also, the selectivity of the other by-products was increased in the temperature range falling outside of 280-300° C.

Test Example 11

Ethanol Yield and Acetic Acid Conversion Depending on Changes in Temperature

Figure 8:
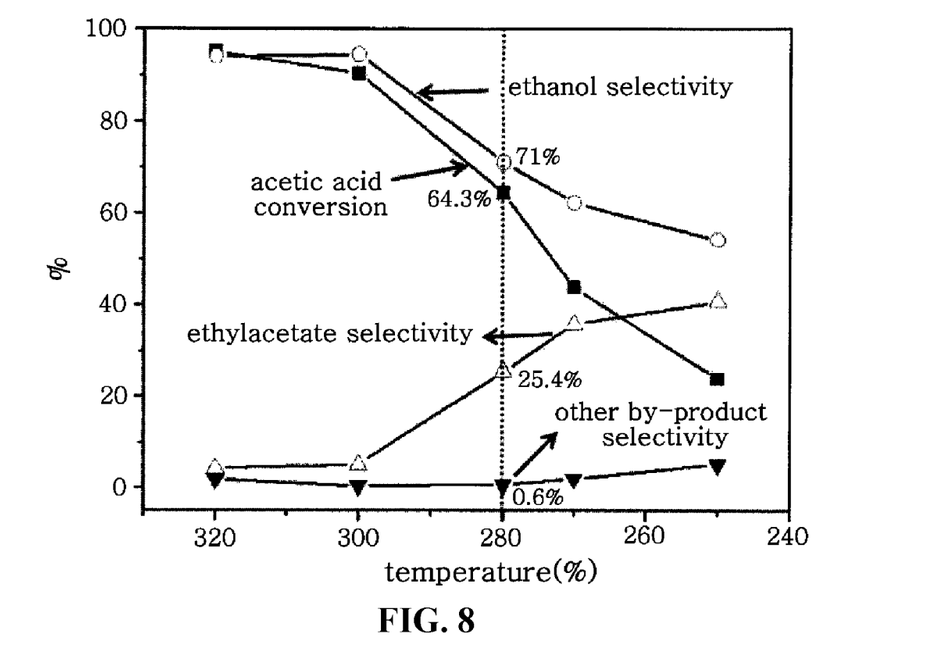
FIG. 8 shows the ethanol yield and the acetic acid conversion depending on changes in temperature.

FIG. 8 shows the results of applying the CZA-541 catalyst of Example 4 to the direct hydrogenation of acetic acid in the temperature range decreased from 320° C. to 240° C. All reactions were performed under conditions of a reaction pressure of 550 psi, acetic acid/hydrogen=57.0, WHSV=0.9. The ethanol selectivity and the acetic acid conversion were about 95% or more in the temperature range of 320-300° C. However, the ethanol selectivity and the acetic acid conversion were drastically decreased in the temperature range of 300° C. or less. The selectivity of ethylacetate which is an esterification product was increased in proportion to the decrease in the reaction temperature.

Unlike the direction hydrogenation of butyric acid as mentioned above, the appropriate reaction temperature was evaluated to be about 300° C. or higher, which is about 20° C. higher than the reaction temperature of the direct hydrogenation of butyric acid. This is considered to be because, in the direct hydrogenation of acetic acid, the energy it takes to activate the carbonyl group of acetic acid is greater than energy that it takes to activate the carbonyl group of butyric acid. Furthermore, the production of ethanol by direct hydrogenation of acetic acid could be judged to be more difficult.

Test Example 12

Direct Hydrogenation of Acid Mixture Including Acetic Acid at Reaction Temperature of 300° C.

Figure 9:
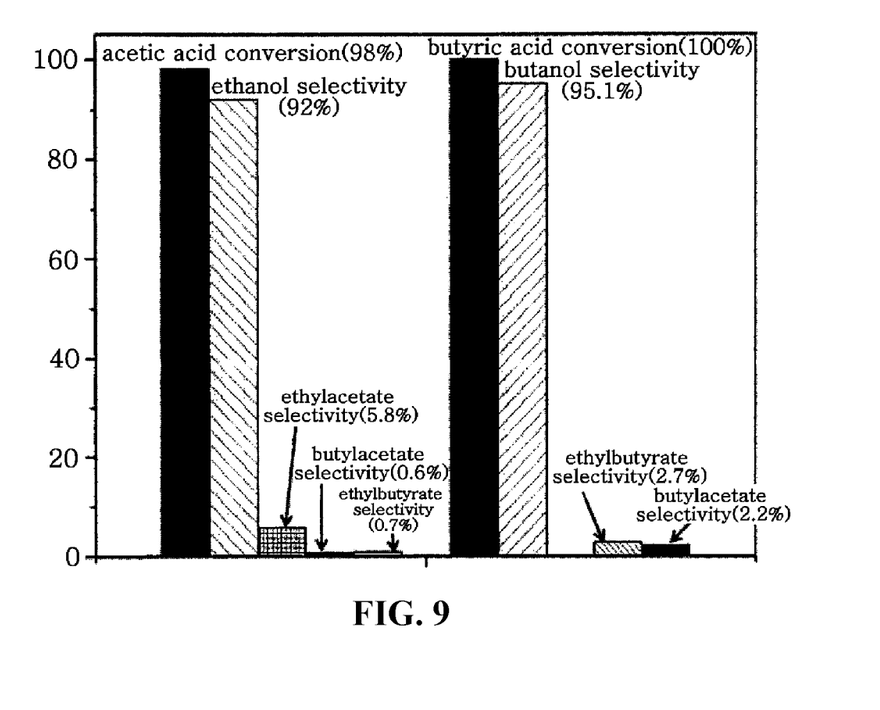
FIG. 9 shows the production of an alcohol mixture from an acid mixture using direct hydrogenation

FIG. 9 shows the results of applying the Cu catalyst of Example 4 to the direct hydrogenation of an acid mixture comprising acetic acid and butyric acid mixed at a molar ratio of 4:1. The reaction was wined out under conditions including a reaction temperature of 300° C., a reaction pressure of 550 psi, and WHSV=0.9, and thus the acetic acid conversion and the ethanol selectivity were lower than the butyric acid conversion and the butanol selectivity.

At the reaction temperature of 300° C., both the carboxylic acid conversion and the alcohol selectivity were expected to be high like when acetic acid and butyric acid were used alone, but by-product selectivity slightly different from the results of direct hydrogenation of respective single acids was obtained. Specifically, butylacetate and ethylbutyrate, which were not shown when acetic acid and butyric acid were used alone, were present, which indicates a mixture resulting from the side-reaction namely esterification of the acids. Thus, compared to when respective acids were used alone under the same temperature and pressure conditions, slightly lower yields of ethanol and butanol resulted.

Also in the acid mixture, the reactivity for acetic acid was lower than for butyric acid, as in the single acids.

Test Example 13

Direct Hydrogenation of Acid Mixture Including Acetic Acid at Reaction Temperature of 280° C.

Table 4 below shows the results of applying the Cu catalyst of Example 4 to direct hydrogenation of an acid mixture comprising acetic acid and butyric acid mixed at a molar ratio of 4:1. The reaction was carried out under conditions including a reaction temperature of 280° C., a reaction pressure of 550 psi, and WHSV=0.9. The results showed that the acetic acid conversion and the ethanol selectivity were lower than the butyric acid conversion and the butanol selectivity.

TABLE 4

| Direct Hydrogenation | Direct Hydrogenation of Single Acid | | Direct Hydrogenation of Acid Mixture | |
|---|---|---|---|---|
| | Acetic Acid | Butyric Acid | Acetic Acid (in Acid Mixture) | Butyric Acid (in Acid Mixture) |
| Acetic Acid Conversion (%) | 64.3 | | 98 | |
| Ethanol Yield (%) | 45.7 | | 87.5 | |
| Butanol Conversion (%) | | 100 | | 97.8 |
| Butanol Yield (%) | | 98.6 | | 89 |

At the reaction temperature of 280° C., both butyric acid and butanol conversions were high when butyric acid was used alone, whereas in the case of acetic acid the conversion and yield were comparatively lower. The results of the direct hydrogenation of the acid mixture at 280° C. showed that the conversion and selectivity of acetic acid in the acid mixture were higher than when acetic acid was used alone. In the direct hydrogenation of carboxylic acid, direct hydrogenation of acetic acid is regarded as the most difficult.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A method of preparing a nano-sized copper based catalyst, comprising:
   dissolving, in an aqueous solution, a first component comprising a copper (Cu) precursor, a second component precursor comprising one or more selected from the group consisting of a transition metal, an alkaline earth metal and a Group IIIb metal, and a third component precursor comprising one or more selected from the group consisting of alumina, silica, silica-alumina, magnesia, titania, zirconia and carbon and then performing stirring, thus obtaining a stirred mixture solution;
   precipitating the stirred mixture solution using Na2CO3 and NaOH, thus forming a catalyst precursor precipitate; and
   washing and filtering the formed catalyst precursor precipitate.

2. The method of claim 1, wherein a ratio of Cu to the second component is set such that the molar ratio of the second component is 0.4-3.5 times that of Cu.

3. The method of claim 1, wherein a molar ratio of Cu to the second component to the third component is 1:0.8-1.5:0.2-0.5.

4. The method of claim 1, wherein the transition metal is Zn, Co, Ni, Cr, Fe, Zn, Co, Ni, Cr, Fe, Mo, Nb, Mn, Pt, Pd, Rh or Ru, the alkaline earth metal is Mg, Ca, Sr or Ba, and the Group IIIb metal is Ga.

5. The method of claim 1, wherein the precipitating is performed at a pH of 5.0-11.0.

6. A nano-sized Cu based catalyst, prepared using the method of claim 1.

7. The Cu based catalyst of claim 6, wherein the Cu based catalyst has a size of 20 nm or less.

8. A nano-sized Cu based catalyst suitable for use in hydrogenation or dehydrogenation, prepared using the method of claim 1.

9. The Cu based catalyst of claim 8, wherein the hydrogenation or dehydrogenation is a water-gas shift reaction, methanol reforming for producing hydrogen from methanol, carbon dioxide hydrogenation for synthesizing methanol from hydrogen and carbon dioxide, hydro-dechlorination for removing chlorine from chlorine-containing hydrocarbon, or production of γ-butyrolactone from 1,4-butanediol (1,4-BDO).

10. A method of preparing alcohol, comprising reacting hydrogen with carboxylic acid comprising a single acid or an acid mixture of two or more acids derived from a microorganism fermented solution, using the nano-sized Cu based catalyst prepared using the method of claim 1.

11. The method of claim 10, wherein the acid mixture is a mixture comprising two or more carboxylic acids selected from among C2-C7 carboxylic acids.

12. The method of claim 10, wherein a flow rate of the hydrogen is 1-100 times that of carboxylic acid based on a molar ratio, and a hydrogen pressure ranges from atmospheric pressure to 100 bar.

13. The method of claim 10, wherein the reacting is performed at a temperature of 200-350° C.

14. The method of claim 10, wherein the acid mixture comprises acetic acid and other carboxylic acids at a molar ratio of 9.0-1.0:1.0.

* * * * *